United States Patent [19]

Nagler et al.

[11] Patent Number: 6,090,814
[45] Date of Patent: Jul. 18, 2000

[54] QUINAZOLINONE-CONTAINING PHARMACEUTICAL COMPOSITIONS FOR PREVENTION OF NEOVASCULARIZATION

[75] Inventors: Arnon Nagler; Shimon Slavin, both of Jerusalem; Israel Vlodavsky, Mevaseret Zion; Mark Pines, Rehovot, all of Israel

[73] Assignees: Agricultural Research Organization Ministry of Agriculture, Bet Dagan; Hadasit Medical Research Services & Development Company, Ltd., Jerusalem, both of Israel

[21] Appl. No.: 09/011,696
[22] PCT Filed: Aug. 12, 1996
[86] PCT No.: PCT/US96/13210
  § 371 Date: May 26, 1998
  § 102(e) Date: May 26, 1998
[87] PCT Pub. No.: WO97/06805
  PCT Pub. Date: Feb. 27, 1997

[30] Foreign Application Priority Data

Aug. 15, 1995 [IL] Israel ......................................... 114951

[51] Int. Cl.[7] .................................................. A61K 31/517
[52] U.S. Cl. ............................................................ 514/259
[58] Field of Search ................................................ 514/259

[56] References Cited

U.S. PATENT DOCUMENTS 3,320,124  5/1967  Walectzky et al. ........................ 167/53
4,340,596  7/1982  Schein ....................................... 424/251
5,449,678  9/1995  Pines, et al. .............................. 514/259

*Primary Examiner*—Phyllis G. Spivack
*Attorney, Agent, or Firm*—Davidson, Davidson & Kappel, LLC

[57] ABSTRACT

The invention provides a composition for attenuating neovascularization comprising administering a pharmaceutically effective amount of a compound of formula I:

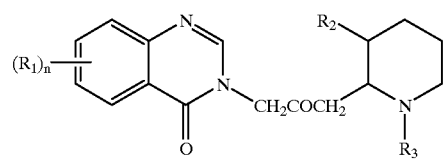

wherein: n=1 or 2;

$R_1$ is a member of the group consisting of hydrogen, halogen, nitro, benzo, lower alkyl, phenyl and lower alkoxy;

$R_2$ is a member of the group consisting of hydroxy, acetoxy, and lower alkoxy, and $R_3$ is a member of the group consisting of hydrogen and lower alkenoxy-carbonyl;

as an active ingredient therein, in combination with a pharmaceutically acceptable carrier.

2 Claims, 6 Drawing Sheets

QUINAZOLINONE-CONTAINING PHARMACEUTICAL COMPOSITIONS FOR PREVENTION OF NEOVASCULARIZATION

BACKGROUND OF THE INVENTION

This application is a 371 of PCT/US96/13210 filed Aug. 12, 1996

The present invention relates to compositions containing quinazolinones. More particularly, the present invention relates to a composition for attenuating vascular endothelial cell proliferation and tube formation and hence angiogenic-associated diseases, as well as for treating human malignancies, i.e., inhibiting primary tumor growth, tumor progression and metastasis, comprising as active ingredient therein a quinazolinone derivative as herein defined.

In U.S. Pat. No. 3,320,124, issued in 1967, there is described and claimed a method for treating coccidiosis with quinazolinone derivatives. Halofuginone, otherwise known as 7-bromo-6-chloro-3-[3-(3-hydroxy-2-piperidinyl)-2-oxopropyl]-4(3H)-quinazolinone, was first described and claimed in said patent by American Cyanamid Company, and was the preferred compound taught by said patent and the one commercialized from among the derivatives described and claimed therein.

Subsequent U.S. Reissue Pat. No. 26,833 and U.S. Pat. Nos. 4,824,847; 4,855,299; 4,861,758 and 5,215,993 all relate to the coccidiocidal properties of halofuginone. U.S. Pat. No. 4,340,596 teaches that halofuginone can also be used for combatting theileriosis.

In 1991, one of the present inventors published an article reporting that reduced collagen synthesis was noted and identified as an important causitive factor in the skin tearing and reduced skin strength of fowl treated with halofuginone, administered in the amounts recommended for use as a coccidiostat. It was also found that, at the cellular level, halofuginone suppressed collagen synthesis by avian skin fibroblasts [I. Granot, et al., *Poult. Sci.*, Vol. 70, pp. 1559–1563 (1991)].

At that time, however, it was neither taught, recognized or suspected that halofuginone or the related quinazolinone derivatives taught in U.S. Pat. No. 3,320,124 could be effectively used for treatment of fibrotic diseases, as well as for treatment of restenosis, glomerulosclerosis, and angiogenesis-dependent diseases.

Clinical conditions and disorders associated with primary or secondary fibrosis, such as systemic sclerosis, graft-versus-host disease (GVHD), pulmonary and hepatic fibrosis and a large variety of autoimrnune disorders, are distinguished by excessive production of connective tissue, which results in the destruction of normal tissue architecture and function. These diseases can best be interpreted in terms of perturbations in cellular functions, a major manifestation of which is excessive collagen deposition.

It is generally recognized that at present, most treatments of fibrotic diseases are ineffective and have little effect upon their inexorable pathological progression. Various attempts have been made in order to reduce collagen deposition in the extracellular space. As is known, progressive fibro-proliferative diseases exhibit excessive production of connective tissues. The crucial role of collagen in fibrosis has prompted attempts to develop drugs that inhibit its accumulation [K. I. Kivirikko, *Annals of Medicine*, Vol. 25, pp. 113–126 (1993)].

Such drugs can act by modulating the synthesis of the procollagen polypeptide chains, or inhibit some specific post-translational events, which will lead either to reduced formation of extra-cellular collagen fibers or to an accumulation of fibers with altered properties. Only a few inhibitors of collagen synthesis are available, despite the importance of this protein in sustaining tissue integrity and its involvement in various disorders.

Cytotoxic drugs have been used in an attempt to slow collagen-producing fibroblast proliferation [J. A. Casas, et al., *Ann. Rhem. Dis.*, Vol. 46, p. 763 (1987)], among them colchicine, which slows collagen secretion into the extracellular matrix [D. Kershenobich, et al., *N. Engl. J. Med.*, Vol. 318, p. 1709 (1988)] and inhibitors of key collagen metabolism enzymes [K. Karvonen, et al., *J. Biol. Chem.*, Vol. 265, p. 8414 (1990); C. J. Cunliffe, et al., *J. Med. Chem.*, Vol. 35, p. 2652 (1992)].

Unfortunately, none of these inhibitors are collagen-type specific. Also, there are serious concerns about the toxic consequences of interfering with biosynthesis of other vital collagenous molecules, such as Clq in the classical complement pathway, acetylcholine esterase of the neuro-muscular junction endplate, conglutinin and pulmonary surfactant apoprotein.

Other drugs which can inhibit collagen synthesis, such as nifedipine and phenytoin, inhibit synthesis of other proteins as well, thereby non-specifically blocking the collagen biosynthetic pathway [T. Salo, et al., *J. Oral Pathol. Med.*, Vol. 19, p. 404 (1990)].

Collagen cross-linking inhibitors, such as β-aminopropionitrile, are also non-specific, although they can serve as useful antifibrotic agents. Their prolonged use causes lathritic syndrome and interferes with elastogenesis, since elastin, another fibrous connective tissue protein, is also cross-linked. In addition, the collagen cross-linking inhibitory effect is secondary, and collagen overproduction has to precede its degradation by collagenase.

In our U.S. Pat. No. 5,449,678, there is described and claimed a method for the treatment of a human patient suffering from a fibrotic condition, restenosis and glomerulosclerosis, comprising administering to the patient a composition comprising a pharmaceutically effective amount of a pharmaceutically active compound of formula I:

wherein: n=1 or 2;

$R_1$ is a member of the group consisting of hydrogen, halogen, nitro, benzo, lower alkyl, phenyl and lower alkoxy;

$R_2$ is a member of the group consisting of hydroxy, acetoxy and lower alkoxy, and

$R_3$ is a member of the group consisting of hydrogen and lower alkenoxy-carbonyl;

effective to inhibit collagen type I synthesis.

After further research and development, it has now been discovered that halofuginone can be used to attenuate neovascularization, as well as for treating human malignancies. It is therefore believed that the other quinazolinone derivatives described and claimed in U.S. Pat. No. 3,320,124, the teachings of which are incorporated herein by reference, have similar properties.

SUMMARY OF THE INVENTION

Thus, according to the present invention, there is now provided a composition for attenuating neovascularization and treating human cancerous tumors, comprising a pharmaceutically effective amount of a compound of formula I:

I wherein: n=1 or 2;
$R_1$ is a member of the group consisting of hydrogen, halogen, nitro, benzo, lower alkyl, phenyl and lower alkoxy;
$R_2$ is a member of the group consisting of hydroxy, acetoxy and lower alkoxy, and
$R_3$ is a member of the group consisting of hydrogen and lower alkenoxy-carbonyl;
as active ingredient therein, in combination with a pharmaceutically acceptable carrier, and the physiologically acceptable salts thereof.

The present invention also provides a method for the treatment of a human patient suffering from protracted angiogensis, comprising administering a pharmaceutically effective amount of a compound of formula I:

I wherein: n=1 or 2;
$R_1$ is a member of the group consisting of hydrogen, halogen, nitro, benzo, lower alkyl, phenyl and lower alkoxy;
$R_2$ is a member of the group consisting of hydroxy, acetoxy and lower alkoxy, and
$R_3$ is a member of the group consisting of hydrogen and lower alkenoxy-carbonyl;
effective for attenuating neovascularization.

The invention further provides a method for the treatment of a human patient suffering from cancerous tumors, comprising administering a pharmaceutically effective amount of a compound of formula I:

I wherein: n=1 or 2;
$R_1$ is a member of the group consisting of hydrogen, halogen, nitro, benzo, lower alkyl, phenyl and lower alkoxy;
$R_2$ is a member of the group consisting of hydroxy, acetoxy and lower alkoxy, and
$R_3$ is a member of the group consisting of hydrogen and lower alkenoxy-carbonyl;
effective for inhibiting the proliferation of cancerous human tumor cells.

Also provided according to the present invention is the use of a compound of formula I in the manufacture of a medicament having neovascular attenuating activity, as described herein.

The invention further provides the use of a compound of formula I in the manufacture of a medicament having an antiproliferative effect on human tumor cells, as described herein.

DETAILED DESCRIPTION OF THE INVENTION

In preferred embodiments of the present invention, said compound is halofuginone.

In U.S. Pat. No. 5,499,678, it is explicitly shown and demonstrated that the compounds of the present invention are effective in the treatment of fibrotic conditions such as scleroderma and GVHD, as well as restenosis and glomerulosclerosis. Such a showing obviates any groundless speculation that the compound may be inactivated before producing an effect; that the compound may not reach the target area, or that other functional properties may make the compound unsuitable for in vivo use. These possibilities, however, are entirely controverted by the very fact that the identical compounds have been shown to be effective in the treatment of two specific fibrotic conditions associated with excessive collagen deposition, i.e., scleroderma and GVHD, as well as restenosis and glomerulosclerosis. Therefore, the teachings of said U.S. Patent Application are incorporated herein by reference.

Referring now to the novel discovery of the present invention, angiogenesis is a complex process in which capillary blood vessels grow in an ordered sequence of events [J. Folkman and M. Klagsbrun, "Angiogenic Factors," *Science*, Vol. 235, pp. 442–447 (1987); J. Folkman and Y. Shing, "Angiogenesis," *J. Biol. Chem.*, Vol. 267, pp. 10931–10934 (1992)]. When a new capillary sprout grows from the side of a venule, endothelial cells degrade basement membrane, migrate toward an angiogenic source, proliferate, form a lumen, join the tips of two sprouts to generate a capillary loop, and manufacture new basement membrane [J. Folkman, "Toward an Understanding of Angiogenesis: Search and Discovery," *Perspectives in Biology and Medicine*, Vol. 29, pp. 1–36 (1985)].

Degradation and remodelling of the ECM are essential processes for angiogenesis. In addition, ECM components synthesized by endothelial cells (i.e., collagens, laminin, thrombospondin, fibronectin and SPARC) function to regulate endothelial cell growth, migration and shape [J. Bischoff, "Approaches to Studying Cell Adhesion Molecules in Angiogenesis," *Trends Cell Biol.*, No. 5, pp. 69–74 (1995)]. It was reported that bovine aortic endothelial cells (BAE) undergoing sprouting and tube formation synthesize type I collagen and SPARC. It was proposed that type I collagen may be involved in directing migration and assembly of the BAE cells [M. L. Iruela-Arispe, et al., *Lab. Invest.*, No. 64, pp. 174–186 (1991)]. It was also found that exogenous type I collagen promoted rapid tube formation by confluent human dermal microvascular endothelial cells [C. J. Jackson and K. L. Jenkins, *Exp. Cell Res.*, No. 192, pp. 319–323 (1991)]. The tubes contained collagen fibrils in the luminal spaces, suggesting that the endothelial cells use the fibrids to fold and align into tube structures.

Whereas extensive neovascularization accompanies embryonic development, in the healthy adult the remarkable ability of existing blood vessels to sprout and reproduce is mostly repressed [J. Folkman and Y. Shing, ibid. (1992)].

Pathological situations exist in which the control mechanisms that normally operate to restrict angiogenesis are broken down, and an uncontrolled growth of blood vessels is unleashed. The resultant, excessive neovascularization underlies a number of so-called "angiogenic diseases" [J. Folkman, "Angiogenesis in Cancer, Vascular, Rheumatoid and Other Diseases," Nature Medicine, Vol. 1, pp. 27–31 (1995)]. One group of angiogenic diseases comprises retinopathies distinguished by excessive ingrowth of blood vessels into the retina, leading to obstruction of vision and eventually to blindness [J. Folkman, ibid. (1995)].

However, the most devastating disease in which unwarranted angiogenesis plays a crucial role is the progression and spread of solid tumors. It is now well-accepted that once tumor take has occurred, every increase in tumor cell population must be preceded by an increase in new capillaries that converge on the tumor and supply the cells with oxygen and nutrients [J. Folkman. ibid. (1985); J. Folkman, "What Is the Evidence that Tumors Are Angiogenesis Dependent?" J. Natl. Cancer Inst., Vol. 82, pp. 4–6 (1989); N. Weidner, et al., "Tumor Angiogenesis Correlates with Metastasis in Invasive Prostate Carcinoma," Amer. J. Pathol., Vol. 143, pp. 401–409 (1993)]. Tumors may thus remain harmless and confined to their tissue of origin, as long as an accompanying angiogenic program is prevented from being activated.

Since the angiogenesis-dependent step in tumor progression is shared by solid tumors of all ethiologies, the ability to inhibit tumor-associated angiogenesis is a most promising approach in combatting cancer [M. S. O'Reilly, et al., "A Novel Angiogenesis Inhibitor that Mediates the Suppression of Metastases by a Lewis Lung Carcinoma," Cell, Vol. 79, pp. 316–328 (1994)].

A substantial body of experimental evidence supports the hypothesis that tumor angiogenesis is fundamental for the growth and metastasis of solid tumors [J. Folkman, ibid. (1989); N. Weidner, et al., ibid. (1993): M. S. O'Reilly, et al., ibid. (1994); N. Weidner, et al., "Tumor Angiogenesis and Metastasis—Correlation in Invasive Breast Carcinoma," N. Eng. J. Med., Vol. 324, pp. 1–8 (1991)]. Indeed, the majority of solid tumors are not even clinically detectable until after the occurrence of neovascularizartion, whose induction in solid tumors is mediated by one or more angiogenic factors [J. Folkman, ibid. (1987); J. Folkman and Y. Shing, ibid. (1992)]. Moreover, the ability to inhibit blood vessel proliferation and penetration into a given organ carries the potential of treating other diseases, which is of paramount medical importance.

Protracted angiogenesis is observed in a variety of pathologic states, such as arthritis, psoriasis, diabetic retinopathy, chronic inflammation, scleroderma, hemangioma, retrolental fibroplasia and abnormal capillary proliferation in hemophiliac joints, prolonged menstruation and bleeding, and other disorders of the female reproductive system [J. Folkman, ibid. (1995); J. W. Miller, et al., "Vascular Endothelial Growth Factor/Vascular Permeability Factor Is Temporarily and Partially Correlated with Ocular Angiogenesis in a Primate Model," J. Pathol., Vol. 145, pp. 574–584 (1994); A. P. Adamis, et al., "Increased Vascular Endothelial Growth Factor Levels in the Vitreous of Eyes with Proliferative Diabetic Retinopathy," Amer. J. Ophthal., Vol. 118, pp. 445–450 (1994); K. Takahashi, et al., "Cellular Markers that Distinguish the Phases of Hemangioma during Infancy and Childhood," J. Clin. Invest., Vol. 93, pp. 2357–2364 (1994); D. J. Peacock, et al., "Angiogenesis Inhibition Suppresses Collagen Arthritis," J. Exp. Med., Vol. 175, pp. 1135–1138 (1992); B. J. Nickoloff, et al., "Aberrant Production of Interleukin-8 and Thrombospondin-1 by Psoriatic Keratinocytes Mediates Angiogenesis," Amer. J. Pathol., Vol. 44, pp. 820–828 (1994); J. Folkman, "Angiogenesis in Female Reproductive Organs," in: Steroid Hormones and Uterine Bleeding, N. J. Alexander and C. d'Arcangues, Eds., American Association for the Advancement of Science Press, Washington, D.C., U.S.A., pp. 144–158 (1992)].

In many of the above-mentioned abnormalities, unrestrained new capillary growth itself contributes to the disease process. For example, in arthritis, new capillaries may invade and destroy joint cartilege. In diabetes, new capillaries in the eye hemorrhage and cause blindness. It is also possible that certain developmental disorders, such as intestinal atresia, vascular malformations, and unilateral fasial atrophy, may be due to angiogenic abnormality [J. Folkman, ibid. (1995)].

Several inhibitors of angiogenesis are being studied; among them are platelet factor 4, the fumagillin-derivate AGH 1470, Interferon α2a, thrombospondin, angiostatic steroids, and angiostatin [J. Folkman, ibid. (1995); M. S. O'Reilly, et al., ibid. (1994); V. Castle, et al., "Antisence-Mediated Reduction in Thrombospondin Reverses the Malignant Pheotype of a Human Squamous Carcinoma," J. Clin. Invest., Vol. 87, pp. 1883–1888; D. Ingber, et al., "Synthetic Analogues of Fumagillin that Inhibit Angiogenesis and Suppress Tumor Growth," Nature, Vol. 348, pp. 555–557].

While the invention will now be described in connection with certain preferred embodiments in the following figures and examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following figures and examples which include preferred embodiments will serve to illustrate the practice of this invention, it being understood that the particulars shown are by way of example and for purposes of illustrative discussion of preferred embodiments of the present invention only, and are presented in the cause of providing what is believed to be the most useful and readily understood description of formulation procedures as well as of the principles and conceptual aspects of the invention.

The results of the experiments carried out are described below with reference to the attached figures, wherein.

EXAMPLES

Experimental Procedures

Cells

Cultures of vascular endothelial cells were established from bovine aorta as previously described [D. Gospodarowicz, et al., "Clonal Growth of Bovine Endothelial Cells: Fibroblast Growth Factor as a Survival Agent," Proc. Natl. Acad. Sci. U.S.A., Vol. 73, p. 4120 (1979)]. Stock cultures were maintained in DMEM (1 g glucose/liter) supplemented with 10% calf serum, 50 U/ml penicillin, and 50 μg/ml streptomycin at 37° C. in 10% $CO_2$ humidified incubators. Partially purified brain-derived bFGF (100 ng/ml) was added every other day during the phase of active cell growth [D. Gospodarowicz, et al., ibid. (1979); I. Vlodavsky, et al., "Vascular Endothelial Cells Maintained in the Absence of Fibroblast Growth Factor Undergo Structural and Functional Alterations that Are Incompatible with Their in Vivo Differentiated Properties," J. Cell Biol., Vol. 83, pp. 468–486 (1979)].

Cell Proliferation: $_3$H-Thymidine Incorporation

Bovine aortic endothelial cells were plated ($4 \times 10_4$ cells/16 mm well) in DMEM supplemented with 10% calf serum. Four days after seeding, the cells were exposed to increasing concentrations of halofuginone (100–500 ng/ml), in the absence or presence of 1 ng/ml bFGF. $_3$H-thymidine (1 μCi/well) was then added for an additional 48 hours, and DNA synthesis was assayed by measuring the radioactivity incorporated into trichloroacetic acid insoluble material [M. Benezra, et al., "Reversal of bFGF Autocrine Cell Transformation by Aromatic Anionic Compounds," Cancer Res., Vol. 52, pp. 5656–5662 (1992); I. Vlodavsky, et al., "Endothelial Cell-Derived Basic Fibroblast Factor: Synthesis and Deposition into Subendothelial Extracellular Matrix," Proc. Natl. Acad. Sci. U.S.A., Vol. 84, pp. 2292–2296 (1987)].

ECM Deposition by Cultured Endothelial Cells

Cultures of bovine corneal endothelial cells were established from steer eyes and maintained as previously described [D. Gospodarowicz, et al., "Stimulation of Corneal Endothelial Cell Proliferation in Vitro by Fibroblast and Epidermal Growth Factors," Exp. Eye Res., No. 25, pp. 75–89 (1977)]. Cells were cultured at 37° C. in 10% $CO_2$ humidified incubators and the experiments were performed with early (3–8) cell passages.

For preparation of sulfate-labelled ECM, corneal endothelial cells were seeded into 4-well plates at a confluent density forming, within 4–6 h, a contact inhibited cell monolayer composed of closely apposed, and growth arrested cells. Under these conditions, the cells remained viable and retained their normal monolayer configuration and morphological appearance up to a concentration of 2 μg/ml halofuginone. $Na_2[^{35}S]O_4$ (540–590 mCi/mmol) was added (40 μCi/ml) one and five days after seeding and the cultures were incubated without medium change. At various intervals after seeding, the subendothelial ECM was exposed by dissolving (5 min., room temperature) the cell layer with PBS containing 0.5% Triton X-100 and 20 mM $NH_4OH$, followed by four washes in PBS [I Vlodavsky, et al., "Lymphoma Cell Mediated Degradation of Sulfated Proteoglycans in the Subendothelial Extracellular Matrix: Relationship to Tumor Cell Metastasis," Cancer Res., Vol. 43, pp. 2704–2711 (1983); I. Vlodavsky, et al., "Endothelial Cell-Derived Basic fibroblast Growth Factor: Synthesis and Deposition into Subendothelial Extracellular Matrix," Proc. Natl. Acad. Sci. USA, Vol. 84, pp. 2292–2296 (1987)]. To determine the total amount of sulfate labelled material, the ECM was digested with trypsin (25 μg/ml, 24 h, 37° C.) and the solubilized material counted in a β-counter.

In Vitro Angiogenesis in Three-Dimensional Gel of Collagen I

Type I collagen was prepared from the tail tendons of adult Sprague-Dawley rats. Briefly, the collagen fibers were solubilized by a slow stirring for 48 h at 4° C. in a sterile, 1/1,000 (v/v) acetic acid solution (300 ml for 1 g of collagen). The resulting solution was filtered through a sterile triple gauze and centrifuged at 16,000 g for 1 h at 4° C. The supernatant was then extensively dialyzed against 1/10 DMEM and stored at 4° C. The collagen matrix gel was obtained by simultaneously raising the pH and ionic strength of the collagen solution. For this purpose,7 vol of collagen solution were quickly mixed with 1 vol of 10× Minimum Essential Medium and 2 vol of sodium bicarbonate (0.15 M).

Thoracic aortas were obtained from 1- to 2-month-old SD rats sacrificed by decapitation [R. F. Nicosia and A. Ottinetti, "Growth of Microvessels in Serum-Free Matrix Culture of Rat Aorta," Lab. Invest., Vol. 63, pp. 115–122 (1990)]. The aortas were immediately transferred to a Petri dish with PBS. The fibro-adipose tissue around the aorta was carefully removed under a dissecting microscope, and 1 mm-long aortic rings were sectioned and extensively rinsed in PBS.

The collagen solution (0.2 ml) was added to each 16-mm well and gellation was allowed for 15 min at 37° C. Each aorta ring was transferred and positioned to the center of the gel and another 0.4 ml of the collagen solution was carefully poured on top of the ring. After the gel was formed, 0.4 ml of serum-free, endothelial growth medium, with or without 0.1 µg/ml halofuginone, was added and the medium was changed every other day.

In Vitro Organization of Endothelial Cells into Capillary-like Networks

Bovine aortic endothelial cells were seeded into 16 mm wells of a 24-well plate and allowed to grow for 24 h, to obtain a subconfluent monolayer. The culture medium was then removed and 0.4 ml of the cold collagen mixture described above were poured on top of the cell monolayer and allowed to polymerize for 10 min at 37° C. Fresh medium (0.6 ml), with or without various concentrations of halofuginone, was added after the collagen had gelled. The reorganization of the endothelial cell monolayer was monitored and photographed with a Zeiss inverted phase contrast photomicroscope [R. Montesano, et al., "In Vitro Rapid Organization of Endothelial Cells into Capillary-like Networks Is Promoted by Collagen Matrices," *J. Cell Biol.*, Vol. 97, pp. 1648–1652 (1983)].

Effect of Halofuginone on Proliferation of Human Leiomyosarcoma Tumor Cells

Samples of human leiomyosarcoma tumors were obtained from women undergoing surgical hysterectomy, as described [R. S. Mangrulker, et al., ibid.]. Minced tissue was placed into 20 ml. cold homogenization buffer: 1 M NaCl, 10mM Tris (pH 7.4), 1 mM EDTA, 1 mM benzamidine, 0.1% CHAPS, 0.01% Aprotinin (Sigma), 10 µg/ml leupeptin, 1 mM AEBSF [R. S. Mangrulker, et al., ibid.]. Samples were homogenized for 2 min and centrifuged at 12000×g for 60 min at 4° C. The supernatants were diluted 1:5 with 10 mM Tris (pH 7.4) to a final volume of 100 ml and filtered with 0.45 µm nylon filters. Cells were plated and maintained in DMEM plus 10% calf serum. The cells remained viable over a number of passages but were used at passages 2 or 3. For proliferation assays, cells were plated in 96-well plates at 10,000 cells/well in 200 µl medium (DMEM with 4.5 g/L glucose, 10% calf serum, 1% glutamine, 1% penicillin/streptomycin) and incubated 2 days until confluent. The medium was changed to DMEM with 0.5% calf serum, 1 µM insulin and 5 µM transferrin. After 24 h, the samples (5–10 µl) were added and after an additional 24 h, [$_3$H]thymidine (1 µCi/well) was added to each well. After 36–48 h incubation, the cells were fixed with methanol, and the DNA was precipitated with 5% trichloroacetic acid. The cells were lysed with 150 µl/well 0.3 N NaOH, transferred to scintillation vials, and counted on a β-counter.

Experimental Results

Antiproliferative Effect of Halofuginone toward Vascular Endothelial Cells

Figure 1A:
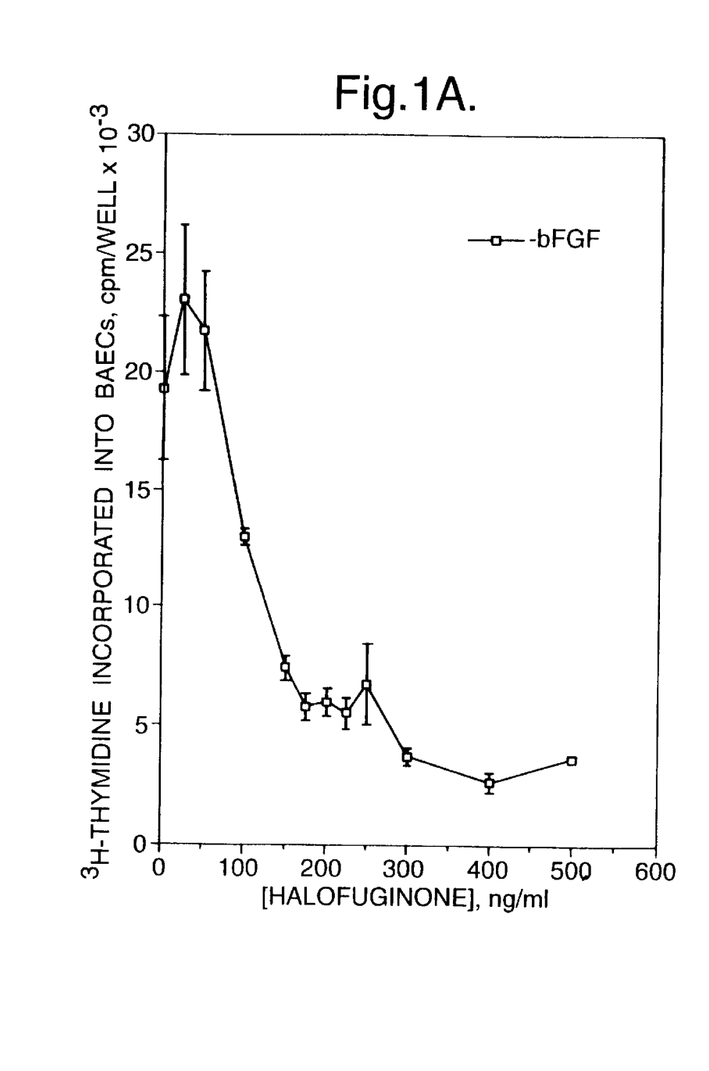
FIGS. 1A and 1B are characteristic dose response curves, showing the effect of halofuginone on $_3$H-thymidine incorporation into bovine aortic endothelial cells maintained in culture, in (FIG. 1A) the absence, or (FIG. 1B) the presence, of 1 ng/ml basic fibroblast growth factor.
Figure 1B:
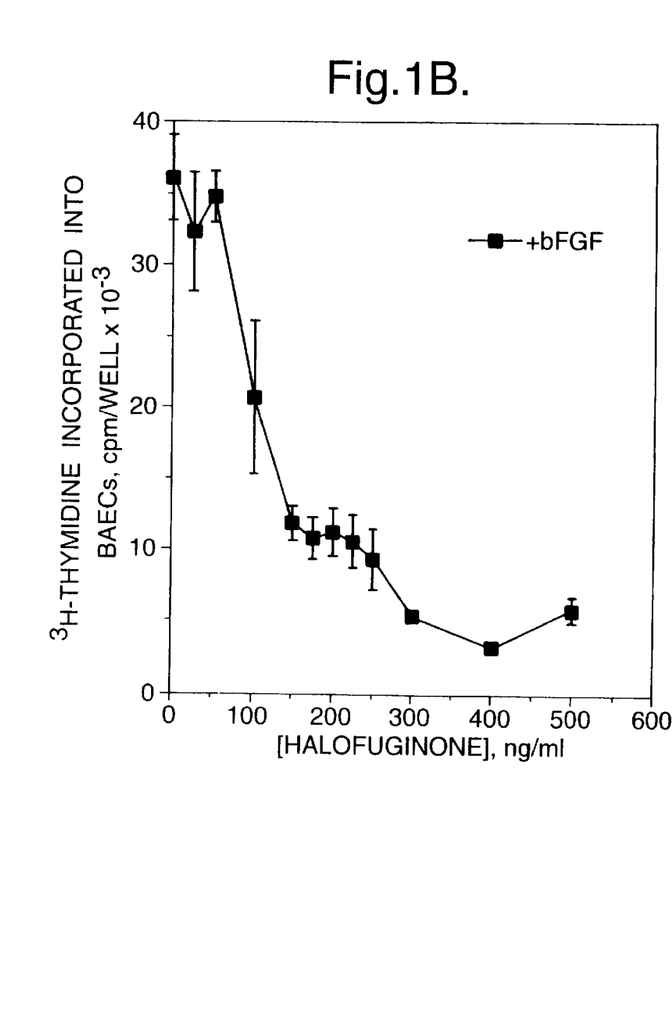

Subconfluent bovine aortic endothelial cells were maintained in medium containing 10% calf serumm in the absence and presence of 1 ng/ml bFGF, with or without increasing concentrations of halofuginone. $_3$H-thymidine was added (1 µCi/well) 4 days after seeding, and DNA synthesis was measured 48 h afterwards. As demonstrated in FIG. 1, 50% inhibition of $_3$thymidine incorporation was obtained at 100 ng/ml halofuginone, regardless of whether or not bFGF (1 ng/ml) was added to the culture medium (FIG. 1).

Effect of Halofuginone on Deposition of ECM by Cultured Endothelial Cells

The subendothelial ECM has been shown to promote migration and proliferation of vascular endothelial cells [D. Gospodarowicz, et al., "The Extracellular Matrix and the Control of Proliferation of Vascular Endothelial and Vascular Smooth Muscle Cells," *J. Supramol. Struc.*, No. 13, pp. 339–372 (1980)]. This activity was attributed to both macromolecular constituents of the ECM and to heparin-binding growth factors such as bFGF that are associated with the GAG side chains of heparan sulfate proteoglycans in the ECM [I. Vlodavsky, et al., "Endothelial Cell-Derived Basic Fibroblast Factor: Synthesis and Deposition into Subendothelial Extracellular Matrix," *Proc. Natl. Acad. Sci. USA*, Vol. 84, pp. 2292–2296 (1987)]. To assess the effect of halofuginone on ECM deposition, labelled sulfate ($Na_2[^{35}S]O_4$) and halofuginone were added to confluent endothelial cell monolayers, 24 h after seeding. At different time periods (day 5, 10 and 14), the cell layer was dissolved in order to expose the underlying ECM. The ECM was then trypsinized and subjected to β-scintillation counting. An almost complete inhibition of sulfate incorporation was observed at 1 µg/ml halofuginone, while 50% inhibition was obtained in the presence of 0.2 µg/ml of the drug.

Organization of Endothelial Cells into Capillary-like Networks

Figure 2A:
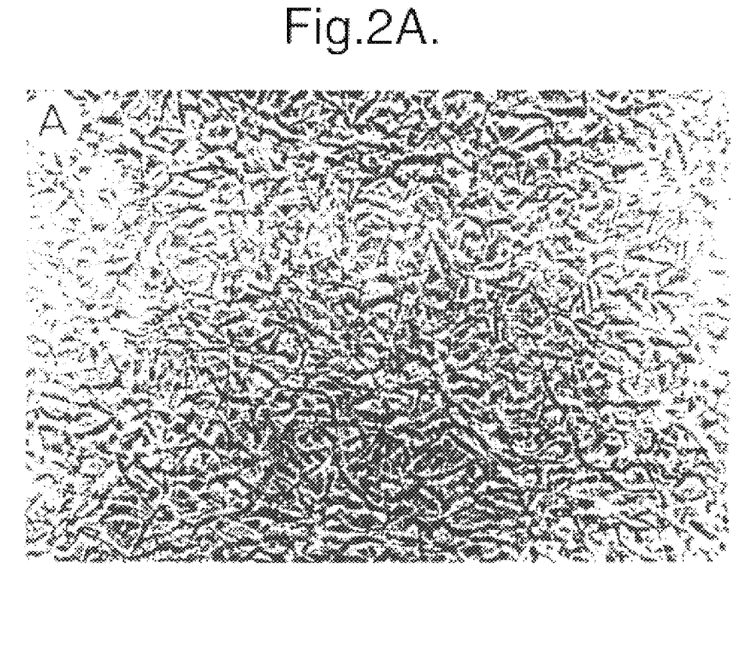
FIG. 2A is a characteristic illustration of the organization of bovine aortic endothelial cells into capillary-like networks. The cell monolayer is covered with a collagen gel and exposed to 1 ng/ml bFGF plus 1 μg/ml heparin. Phase contrast micrographs were taken after 2 days in culture. The cells reorganized into a network of branching and anastomosing capillary-like tubes.
Figure 2B:
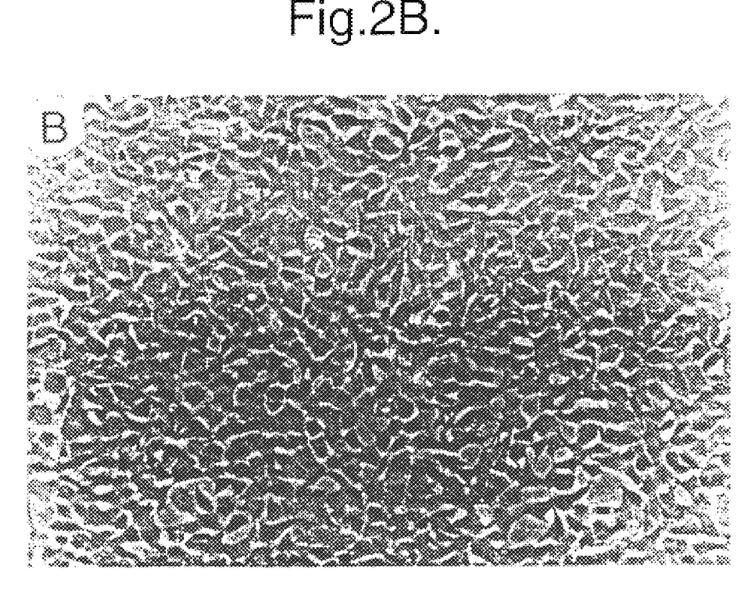
FIG. 2B shows the endothelial cell cultures of FIG. 2A following incubation with 0.1 μg/ml halofuginone. The cells maintained a non-overlapping, monolayer arrangement and failed to form the typical branching and anastomosing capillary-like tubes.

Bovine aortic endothelial cells were seeded into 16 mm wells of a 24-well plate and allowed to grow on the surface of the gels for 24 h, to obtain a subconfluent monolayer. The culture medium was then removed and 0.4 ml of a cold collagen were poured on top of the cell monolayer and allowed to polymerize. Fresh medium containing bFGF (1 ng/ml) and heparin (1 µg/ml), with (FIG. 2B) or without (FIG. 2A) 0.1 µg/ml of halofuginone, was added after the collagen had gelled [R. F. Nicosa and A. Ottinetti, "Growth of Microvessels in Serum Free Matrix Culture of Rat Aorta," *Lab. Invest.*, Vol. 63, pp. 115-122 (1990)]. As is demonstrated in FIG. 2B, halofuginone completely inhibited the invasion of the endothelial cells into the collagen gel and their subsequent organization into a network of branching and anastomosing capillary-like tubes.

Microvessel Formation

Figure 3A:
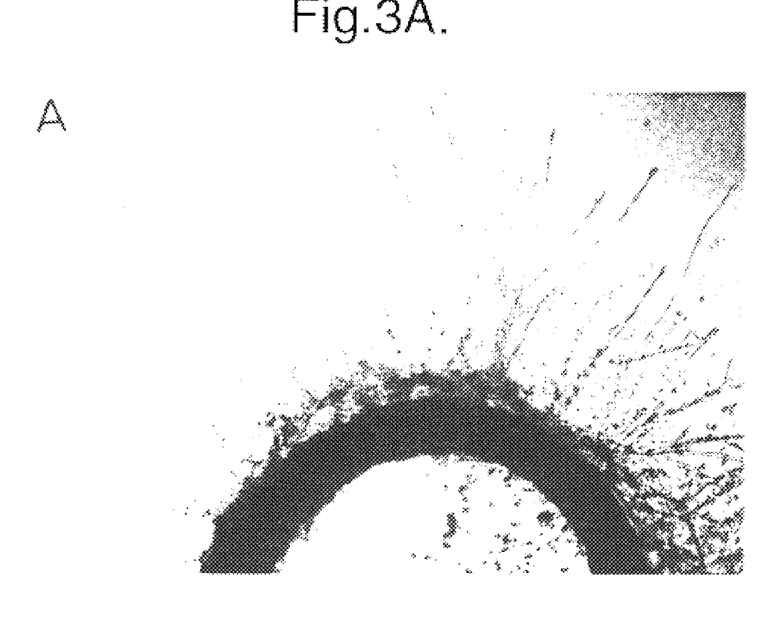
FIG. 3A is a characteristic illustration of newly formed (day 10) microvessels branching from rat aortic rings embedded in Type I collagen gel, giving rise to loops and networks.
Figure 3B:
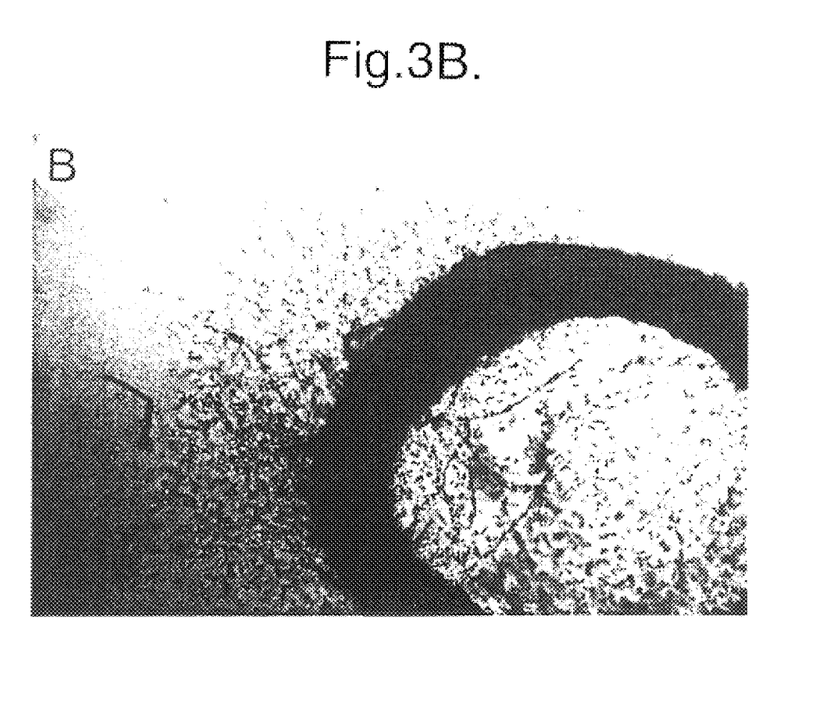
FIG. 3B shows the rat aortic rings of FIG. 3A, following incubation with 0.1 μg/ml halofuginone, which was replaced every other day. Single cells migrated from the aortic ring toward the periphery, but failed to align into microvessel tubes.
Figure 4:
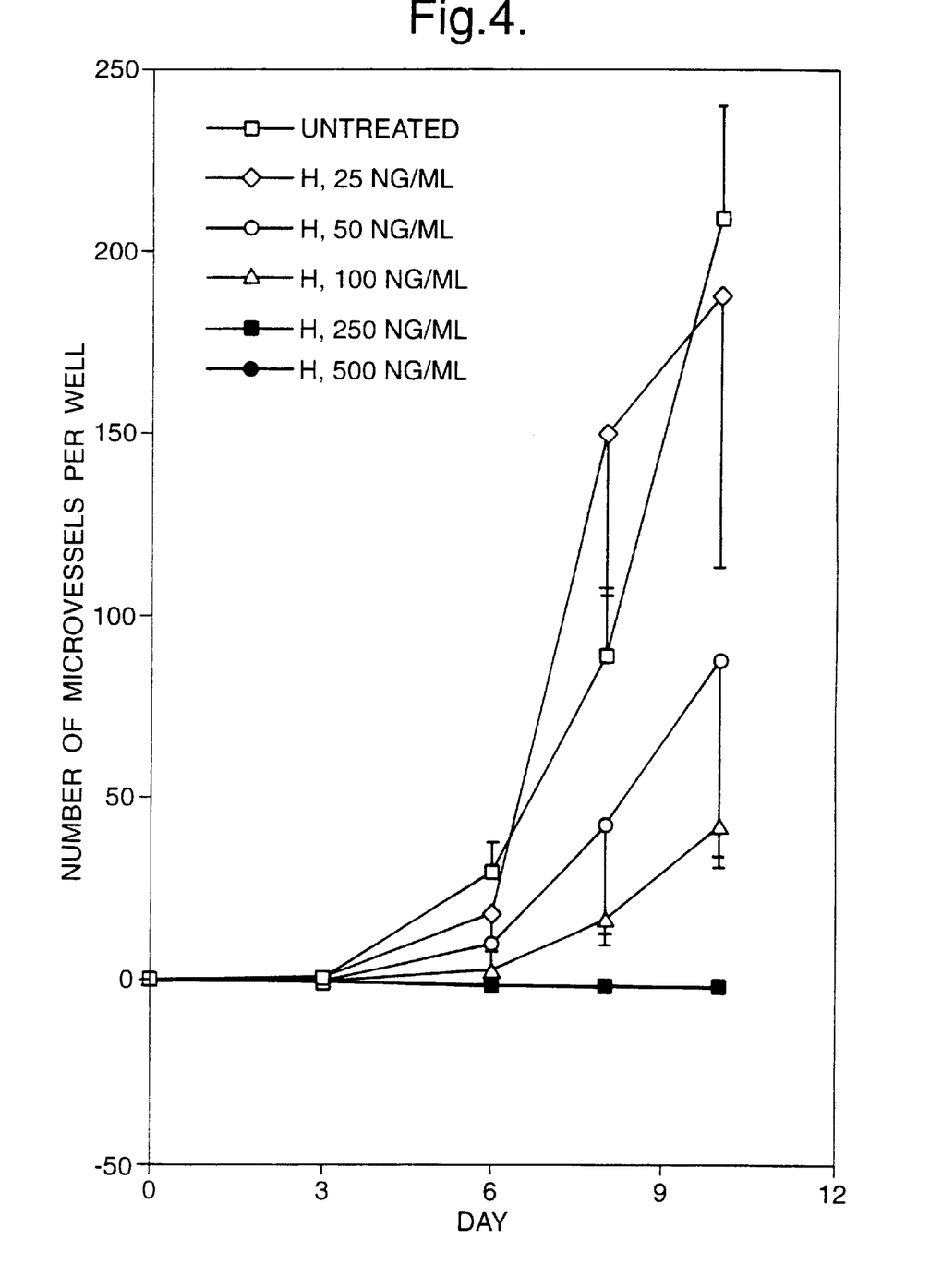
FIG. 4 is a characteristic curve showing the time and dose response of the inhibitory effect of halofuginone on microvessel formation, using the collagen Type I embedded rat aortic ring assay of FIG. 3.

Thoracic aortas were obtained from 1- to 2-month old SD rats sacrificed by decapitation [R. F. Nicosia, et al., ibid. (1990)]. The aortas were transferred to a Petri dish and 1 mm-long aortic rings were sectioned and extensively rinsed in PBS. Type I collagen solution was added to each 16 mm well, and gellation was allowed for 15 min at 37° C. Another 0.4 ml of the collagen solution was poured on top of the ring. After the gel was formed, serum-free endothelial growth medium, with or without 0.1 µg/ml halofuginone, was added and the medium was changed every other day. FIG. 3A shows the culture at day 10, when the newly-formed branching microvessels were developed from the end of resection of the aorta, giving rise to loops and networks. FIG. 3B shows the same culture treated with 0.1 µg/ml halofuginone, replaced every other day. Under these conditions, single cells were migrating from the aortic ring toward the periphery, but failed to align into microvessel tubes. FIG. 4 is a dose response quantitation of this effect.

Figure 5:
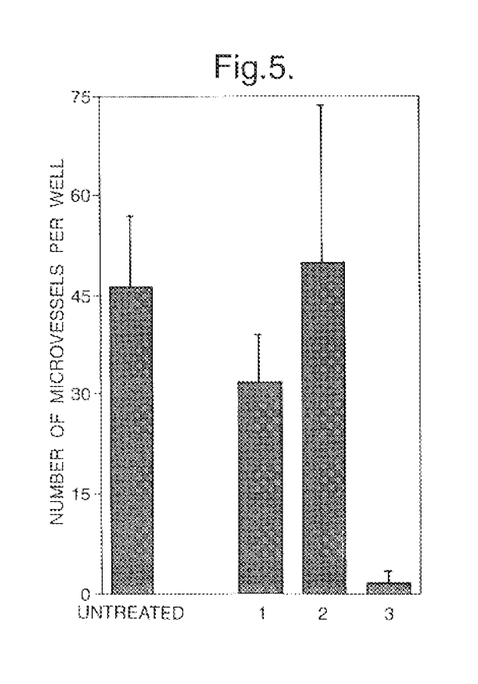
FIG. 5 is a characteristic bar graph showing that removal of halofuginone (250 ng/ml) on day 2 (1) or 6 (2) resulted in microvessel formation (evaluated on day 14) similar to that observed with untreated aortic rings (untreated). Complete inhibition of microvessel formation was obtained when halofuginone was present throughout the 14-day incubation period (3).
Figure 6:
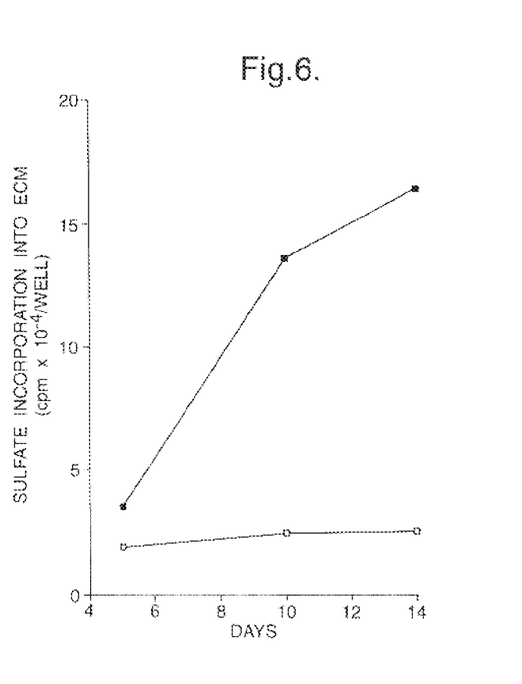
FIG. 6 is a characteristic curve demonstrating the effect of halofuginone on sulfate incorporation into the subendothelial ECM. Bovine corneal endothelial cells were seeded at a confluent cell density and exposed to 1 μg/ml halofuginone (□) in the presence of $Na_2[^{35}S]O_4$. Control cells (■) were maintained in the absence of halofuginone. At different time points, the cell layer was solubilized to expose the underlying ECM, digested with trypsin and the solubilized material counted in a β-scintillation counter.

An almost complete inhibition of microvessel formation was obtained at 100 ng/ml halofuginone (FIG. 4). Complete inhibition was observed in the presence of 250 ng/ml halofuginone, but removal of the drug on day 2 or 6 resulted in microvessel formation, similar to that seen with untreated aortic rings (FIG. 5).

Antiproliferative Effect of Halofuginone toward Human Leiomyosarcoma Tumor Cells The effect of halofuginone on proliferation of human leiomyosarcoma tumor cells was investigated. Leiomyosarcoma tumors have abundant extracellular matrix and are also well vascularized [A. Ferenczy, et al., "A Comparative Ultrastructural Study of Leiomyosarcoma, Cellular Leiomyoma, and Leiomoma of the Uterus," *Cancer*, No. 28, pp. 1004–1018 (1971)]. Their growth is thought to be dependent on growth factors (i.e., bFGF, HB-EGF) produced by normal and malignant myometrial cells [A. Zhang, et al., "Heparin-Binding Epidermal Growth Factor-Like Growth Factor is Differentially Regulated by Progesterone and Estradiol in Rat Uterine Epithelial and Stromal Cells," *Endocrinology*, No. 134, pp. 1089–1094 (1994); R. S. Mangrulker, et al., "Isolation and Characterization of Heparin-Binding Growth Factors in Human Leiomyomas and Normal Myometrium," *Biology of Reproduction*, No. 53, pp. 636–646 (1995)] and locally embedded in the surrounding ECM [I. Vlodavsky, et al., "Extracellular Matrix-Bound Growth Factors. Enzymes and Plasma Proteins," in: *Basement Membranes: Cellular and Molecular Aspects*, D. H. Rohrbach and R. Timpl, Eds., Academic Press, Inc., Orlando, Fla., U.S.A., pp. 327–343 (1993)].

Subconfluent human leiomyoma tumor cells were seeded in medium containing 10% fetal calf serum (FCS). 24 h after seeding, increasing concentrations of halofuginone (10–100 ng/ml) were added and 24 h later the cells were exposed to $_3$H-thymidine (1 µCi/well). DNA synthesis was measured 48 h afterwards. As demonstrated in FIG. 7A, 60–70% inhibition of $_3$H-thymidine incorporation was obtained at 2.5 ng/ml halofuginone.

Figure 7A:
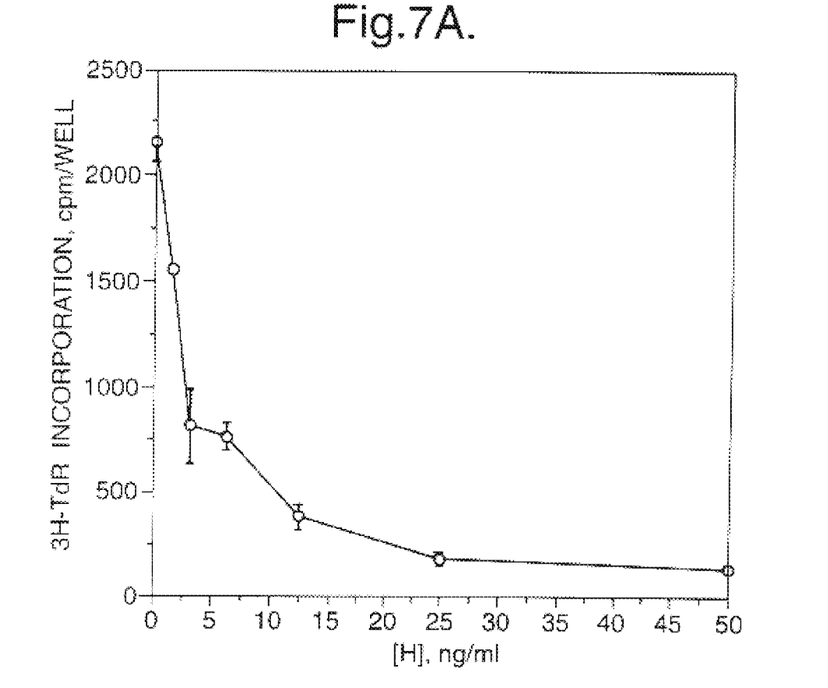
FIG. 7A is a characteristic curve showing the effect of halofuginone on $_3$H-thymidine incorporation into actively growing, subconfluent, human leiomyosarcoma tumor cells.
Figure 7B:
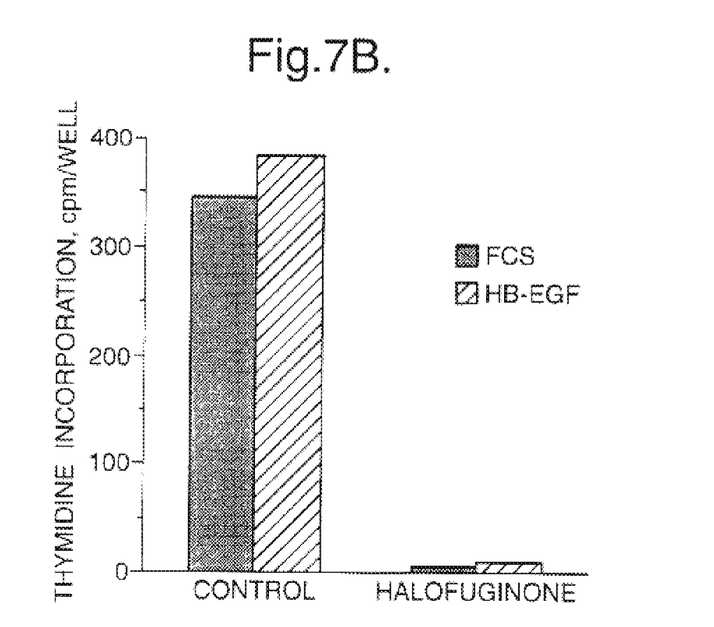
FIG. 7B compares growth arrested leiomyosarcoma cells stimulated to proliferate in response to 10% FCS (■) or 10 ng/ml HB-EGF (▨) in the absence or presence of 10 ng/ml halofuginone.

Resting human leiomyoma tumor cells are induced to proliferate in response to FCS or heparin-binding epidermal growth factor (HB-EGF). The leiomyosarcoma tumor cells were growth-arrested by 48 h incubation in medium containing 0.5% FCS.1. The cells were then exposed (24 h) to either 10% FCS or 10 ng/ml HB-EGF in the absence or presence of 10 ng/ml halofuginone. $_3$H-thymidine was then added and DNA synthesis measured 36 h later. A complete inhibition of cell proliferation induced by both serum or HB-EGF was observed in the presence of halofuginone (FIG. 7B).

Conclusions

The present invention, in its most preferred embodiment, utilizes a highly potent, inexpensive and non-toxic compound which inhibits several components participating in neovascularization. For example, halofuginone inhibits the proliferation of both vascular endothelial cells and smooth muscle cells [E. F. Choi, et al., "Halofuginone, A Specific Collagen Type I Inhibitor, Reduces Anastomotic Intimal Hyperplasia," *Arch. Surg.*, Vol. 130, pp. 257–261 (1995)], as well as the synthesis of collagen [I. Granot, et al., "Halofugcinone: An Inhibitor of Collagen Type I Synthesis," *Biochem. Biophys. Acta*, Vol. 1156, pp. 107–112 (1993)] and assembly of the sub-endothelial ECM, which are all essential for microvessel tube formation [J. Folkman and M. Klagsbrun, ibid. (1987); J. Folkman and Y. Shing, ibid. (1992); J. Folkman, ibid. (1985)]. Some of the current approaches to inhibit angiogenesis utilize agents such as anti-integrin antibodies or signal transduction inhibitors which are likely to exert a broad spectrum of effects [J. Folkman, ibid. (1995); P. C. Brooks. et al., "Integrin αvβ3 Antagonists Promote Tumor Regression by Inducing Apoptosis of Angiogenic Blood Vessels," *Cell*, Vol. 79, pp. 1157–1164 (1994)] and hence may have potential side effects. Halofuginone, on the other hand, has a relatively narrower and a more specific mode of action. In addition, many of the compounds that are now being evaluated as antiangiogenic agents are proteins, e.g., antibodies, thrombospondin, angiostatin, platelet factor IV [J. Folkman, ibid. (1995); M. S. O'Reilly, et al., *ibid.* (1994); V. Castle, et al., *ibid.*; P. C. Brooks, et al., ibid. (1994)], which are readily degraded in the body and hence should be administered in high doses and frequencies.

The approach of the present invention utilizes a highly potent, inexpensive and non-toxic compound. Moreover, halofuginone is a low molecular weight compound which in all likelihood can be administered orally. The compound has been approved by the F.D.A. for use in treating farm animals. These characteristics make halofuginone a most promising, clinically useful drug for inhibiting neovascularization and tumor angiogenesis.

The use of halofuginone as a non-toxic compound which efficiently inhibits blood vessel formation is expected to provide an effective strategy for inhibiting tumor growth and spread, as well as for treating various clinical disorders with protracted angiogenesis, as described above.

In the above, it has also been demonstrated that halofuginone at exceedingly low concentration (2.5 ng/ml) exerts an almost complete inhibition of DNA synthesis in human leiomyosarcoma tumor cells, regardless of whether the cells are stimulated by serum or by a potent growth-promoting factor such as HB-EGF. This concentration of halofuginone is 40-fold lower than the concentration required to inhibit the proliferation of normal vascular endothelial cells, indicating a direct and highly potent antiproliferative effect of halofuginone on the leiomyosarcoma tumor cells.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for attenuating neovascularization, comprising administering to a human patient a pharmaceutically effective amount of a compound of formula I:

wherein: n=1 or 2;
$R_1$ is a member of the group consisting of hydrogen, halogen, nitro, benzo, lower alkyl, phenyl and lower alkoxy;
$R_2$ is a member of the group consisting of hydroxy, acetoxy, and lower alkoxy, and
$R_3$ is a member of the group consisting of hydrogen and lower alkenoxy-carbonyl; effective for attenuating neovascularization.

2. A method according to claim 1, wherein said compound is halofuginone.

* * * * *